(12) United States Patent
Ninomiya et al.

(10) Patent No.: US 8,955,570 B2
(45) Date of Patent: Feb. 17, 2015

(54) ABSORBENT STRUCTURE MANUFACTURING APPARATUS

(75) Inventors: Akihide Ninomiya, Kagawa (JP);
Kazuo Ukegawa, Kagawa (JP)

(73) Assignee: Unicharm Corporation, Ehime (JP)

( * ) Notice: Subject to any disclaimer, the term of this patent is extended or adjusted under 35 U.S.C. 154(b) by 345 days.

(21) Appl. No.: 13/579,971

(22) PCT Filed: Feb. 25, 2011

(86) PCT No.: PCT/JP2011/054400
§ 371 (c)(1),
(2), (4) Date: Oct. 11, 2012

(87) PCT Pub. No.: WO2011/105587
PCT Pub. Date: Sep. 1, 2011

(65) Prior Publication Data
US 2013/0025792 A1  Jan. 31, 2013

(30) Foreign Application Priority Data
Feb. 26, 2010  (JP) .................. 2010-043411

(51) Int. Cl.
*B32B 41/00* (2006.01)
*A61F 13/15* (2006.01)

(52) U.S. Cl.
CPC .............. *A61F 13/15658* (2013.01)
USPC ................... 156/361; 156/366; 156/378

(58) Field of Classification Search
CPC ............ B02C 2013/28663; B28B 2038/0024;
B28B 38/18; B28B 41/00; B28B 41/02;
D01G 7/06; D21B 1/061; D21B 1/066;
D21B 1/068; D21C 7/02; G05G 15/06
USPC ............. 156/352, 361, 366, 377; 162/20, 28,
162/259, 262, 267; 19/145.5; 198/463.4
See application file for complete search history.

(56) References Cited

U.S. PATENT DOCUMENTS

2003/0134559 A1* 7/2003 Delzer et al. .................. 442/394
2003/0234069 A1* 12/2003 Coenen et al. .................. 156/64

(Continued)

FOREIGN PATENT DOCUMENTS

| JP | 54126358 A | 10/1979 |
| JP | 55016185 U | 2/1980 |
| JP | 57053429 U | 3/1982 |
| JP | 58002134 A | 1/1983 |
| JP | 2214572 A | 8/1990 |
| JP | 2252561 A | 10/1990 |
| JP | 8215629 A | 8/1996 |

(Continued)

OTHER PUBLICATIONS

International Search Report and Written Opinion for PCT/JP2011/054400, dated May 31, 2011.

*Primary Examiner* — George Koch
(74) *Attorney, Agent, or Firm* — Lowe Hauptman & Ham LLP (57) ABSTRACT

An absorbent structure manufacturing apparatus has a feeder that includes a measuring roller provided with a filling region to be filled with absorbent discrete material, a material feeding space to reserve and feed the absorbent material to the filling region, a scraper located downstream of the material feeding space to scrape surplus amount of the absorbent material fed to the filling region, a feed chute to receive and retain temporarily the absorbent material from the filling region, and an open-close movable shutter on a peripheral wall of the feed chute. The measuring roller is rotary driven by a rotary drive and the shutter is opened-closed by an actuator. The rotary drive is rotated at a velocity corresponding to a conveyance velocity of a continuous sheet and the actuator controls the shutter in timing corresponding to the conveyance velocity. The absorbent material is fed onto the continuous sheet.

8 Claims, 11 Drawing Sheets

(56) References Cited

U.S. PATENT DOCUMENTS

| | | | |
|---|---|---|---|
| 2006/0021695 A1* | 2/2006 | Blessing et al. | 156/196 |
| 2006/0153984 A1 | 7/2006 | Suzuki et al. | |
| 2010/0173078 A1 | 7/2010 | Suzuki et al. | |
| 2010/0173080 A1 | 7/2010 | Suzuki et al. | |

FOREIGN PATENT DOCUMENTS

| | | |
|---|---|---|
| JP | 2004000830 A | 1/2004 |
| JP | 2007050380 A | 3/2007 |
| JP | 2008154964 A | 7/2008 |
| JP | 2009106861 A | 5/2009 |
| WO | 2004062816 A1 | 7/2004 |

* cited by examiner

ABSORBENT STRUCTURE MANUFACTURING APPARATUS

RELATED APPLICATIONS

The present application is a National Phase of International Application Number PCT/JP2011/054400, filed Feb. 25, 2012, and claims priority from Japanese Application Number 2010-043411, filed Feb. 26, 2010.

TECHNICAL FIELD

The present invention relates to absorbent structure manufacturing apparatuses and, more specifically, to absorbent structure manufacturing apparatuses adapted for intermittent feeding of absorbent discrete material such as fluff wood pulp and superabsorbent polymer particles usually used as the material for sanitary articles such as disposable diapers and sanitary napkins onto predetermined positions on a continuous sheet being conveyed by a conveyor.

BACKGROUND

Conventionally, absorbent structure manufacturing apparatuses adapted for intermittent feeding of absorbent discrete materials onto the predetermined positions on a continuous sheet being conveyed in the machine direction are known. For example, JP 2009-106861 A (PTL 1) discloses an absorbent structure manufacturing apparatus including a conveyor belt used to convey continuous sheet, a roller rotating at a same velocity as that of the conveyor belt and having grooves to retain therein absorbent discrete material and an intermittent feeder serving for intermittent feed of the absorbent discrete material onto the roller. JP H2-214572 A (PTL 2) discloses an absorbent structure manufacturing apparatus including a roller provided with grooves adapted to retain therein absorbent discrete material and a fork slidably cooperating with these grooves.

CITATION LIST

Patent Literature

{PTL 1}: JP 2009-106861 A
{PTL 2}: JP H2-214572 A

SUMMARY

Technical Problem

In the absorbent structure manufacturing apparatus disclosed in PTL 1, the absorbent and dispersible material having been fed from the feeder to the roller is retained in the grooves formed on the outer peripheral surface of the roller and then is evenly and intermittently fed directly onto the continuous sheet so that a defined arbitrary feed pattern may be stably formed. In the absorbent structure manufacturing apparatus disclosed in PTL 2, the fork includes an angular aperture adjusting mechanism and the amount of the absorbent discrete materials to be fed may be selectively controlled by adjusting the angular aperture.

However, in the absorbent structure manufacturing apparatus disclosed in PTL 1, the grooves have a predetermined pattern shape and the amount of the absorbent discrete material filled in the respective grooves, the shape as well as the size of the respective filling target regions are predetermined. In consequence, it is difficult to adjust the amount of the absorbent discrete material to be fed and the feed target region. In addition, when the kind of the absorbent discrete material is changed and the size and/or the shape of the particles is/are changed, it is impossible for the existing roller to feed the predetermined amount of the absorbent discrete material. To feed the predetermined amount of a different type of the absorbent discrete material, the existing roller need to be changed to a new roller having grooves adapted for the size and shape or the like of such a different kind of absorbent discrete material.

In the absorbent structure manufacturing apparatus disclosed in PTL 2, when the feed rate and/or the feed target region of the absorbent discrete material are changed, distal ends of the fork should be thrust into the grooves as the case may be and there is a possibility that the distal ends of the fork might be unacceptably worn away and make it difficult to continue the production. In addition, the grooves extend in the machine direction, i.e., in the circumferential direction of the roller and, in consequence, the absorbent discrete material filled in the grooves may spill out due to rotation of the roller. For this reason, continuous feed of the predetermined amount of the absorbent discrete material onto the given position on the continuous sheet might be difficult.

An object of the present invention is to provide an absorbent structure manufacturing apparatus including a feeder improved so that the feed amount as well as the feed target region of the absorbent discrete material may be adjusted and, even when the kind of the absorbent discrete material is changed, the predetermined amount may be intermittently fed without changing the existing measuring roller to another measuring roller.

Solution to Problem

According to the present invention, there is provided an absorbent structure manufacturing apparatus including a feeder adapted for intermittent feeding of an absorbent discrete material onto a continuous sheet continuously conveyed in a machine direction.

In the absorbent structure manufacturing apparatus of this invention,
  the feeder includes:
    a measuring roller rotating in one direction and provided on an outer peripheral surface thereof with a filling region adapted to be filled with a predetermined amount of the absorbent discrete material;
    a material feeding space adapted to reserve the absorbent discrete material on a steady basis and to feed the absorbent discrete material to the filling region of the measuring roller;
    a scraper located downstream of the feeder in the one direction so as to extend along a part of the outer peripheral surface of the measuring roller to fill the filling regions with only a predetermined amount of the absorbent discrete material fed in surplus to the filling region;
    a feed chute adapted for receiving and temporarily retaining the absorbent discrete material having filled in the filling region and an open-close movable shutter forming a part of a peripheral wall defining the feed chute,
  wherein:
    the measuring roller is rotary driven by rotary drive means in the one direction through the intermediary of a rotary shaft;
    the shutter is opened and closed under control of open-close actuator means;
    the rotary drive means and the open-close actuator means are electrically controlled by a control unit so that the rotary drive means rotates at a velocity corresponding to a conveyance velocity of the continuous sheet;

the open-close actuator means operates in association with the rotary drive means to open-close the shutter in a timing corresponding to the conveyance velocity; and the absorbent discrete material temporarily retained in the feed chute is intermittently fed onto the continuous sheet.

The terms "absorbent discrete material" used herein means superabsorbent polymer particles and/or fluff wood pulp (comminuted pulp) and other similar materials usually used in disposable diapers, sanitary napkins or the like to absorb and to contain human body waste such as urine or menstrual blood.

According to one embodiment of this invention, the filling region is defined by a plurality of filling grooves extending in a direction crossing the machine direction.

According to another embodiment of this invention, the filling grooves are continuously arranged on the outer peripheral surface of the measuring roller in a circumferential direction thereof.

According to still another embodiment of this invention, the apparatus includes a velocity detector means adapted to detect the conveyance velocity of the continuous sheet so that the conveyance velocity detected by the velocity detector means is input to the control unit and a control signal in response to the conveyance velocity is transmitted from the control unit to the rotary drive means and the open-close actuator means.

According to yet another embodiment of this invention, the rotary drive means is a servomotor.

According to further another embodiment of this invention, the feed chute and the shutter are respectively divided into two or more sections in the cross direction so that the absorbent discrete material may be fed onto the continuous sheet intermittently in the machine direction as well as in the cross direction.

According to one alternative embodiment of this invention, the filling region defined on the measuring roller and the scraper are divided into two or more sections in the cross direction so that the feed chute and the scraper are respectively divided into two or more sections in the cross direction and the feed chute and the shutter are respectively divided into two or more sections so as to correspond to the respective sections of the divided filling region.

According to another alternative embodiment of this invention, the continuous sheet is conveyed by a rotary drum so that at least a step of feeding the absorbent discrete material by the feeder and a step of bonding another continuous sheet to the continuous sheet may be carried out on the rotary drum.

Advantageous Effects of Invention

In the absorbent structure manufacturing apparatus according to this invention, the rotary drive means adapted to rotary drive the measuring roller of the feeder and the open-close actuator means adapted to open-close the shutter are electrically controlled so that these means may be driven and actuated in accordance with the conveyance velocity of the continuous sheet. In consequence, the amount of the absorbent discrete material to be fed and the feed target region may be easily adjusted and, even when the kind of the absorbent discrete material is changed, the predetermined amount thereof may be fed onto the continuous sheet without changing the measuring roller.

BRIEF DESCRIPTION OF DRAWINGS

FIG. 4($a$) is a perspective view of a measuring roller and FIG. 4($b$) is a sectional view taken along line IV-IV in FIG. 4($a$).

FIG. 6($a$) is a partially scale-enlarged diagram illustrating open-close controlling means and FIG. 6($b$) is a partially cutaway sectional view of the open-close controlling means.

DESCRIPTION OF EMBODIMENTS

<First Embodiment>

Figure 1:
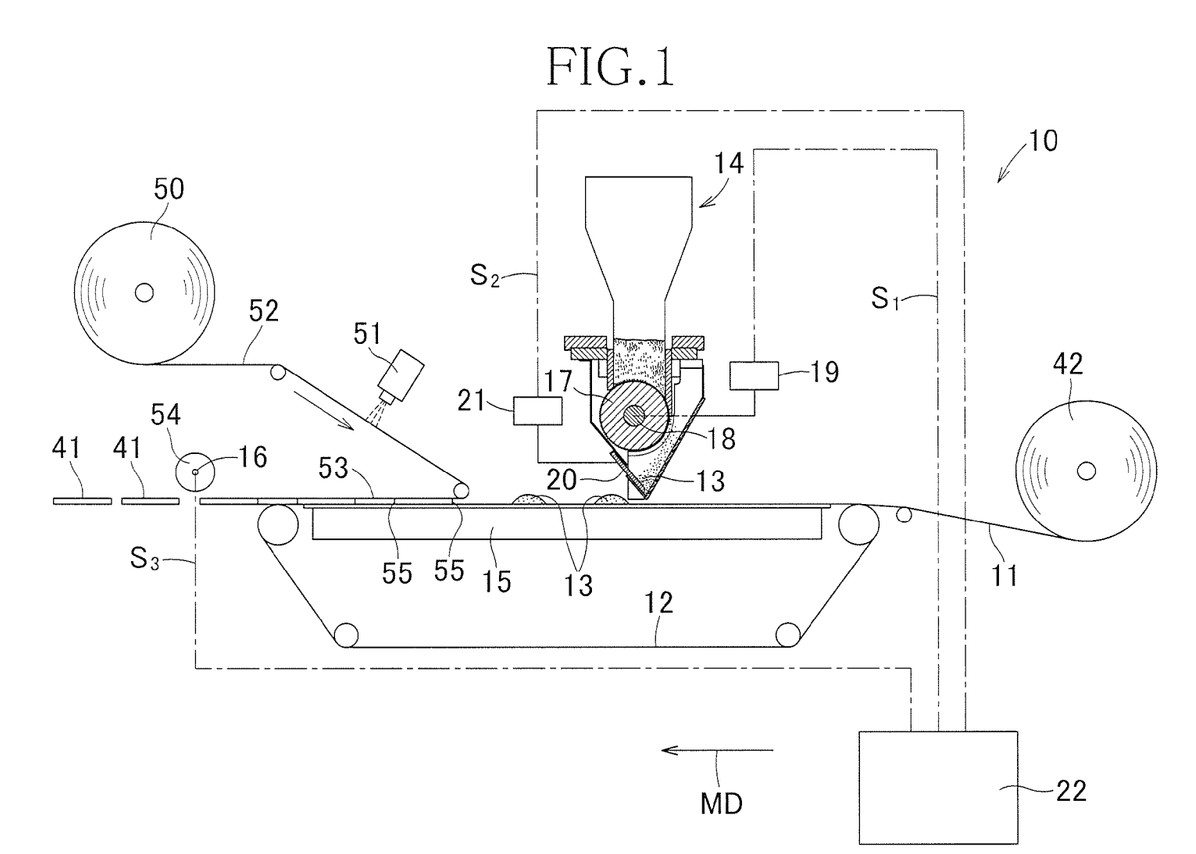
FIG. 1 is a diagram schematically illustrating an absorbent structure manufacturing apparatus according to a first embodiment of this invention.
Figure 2:
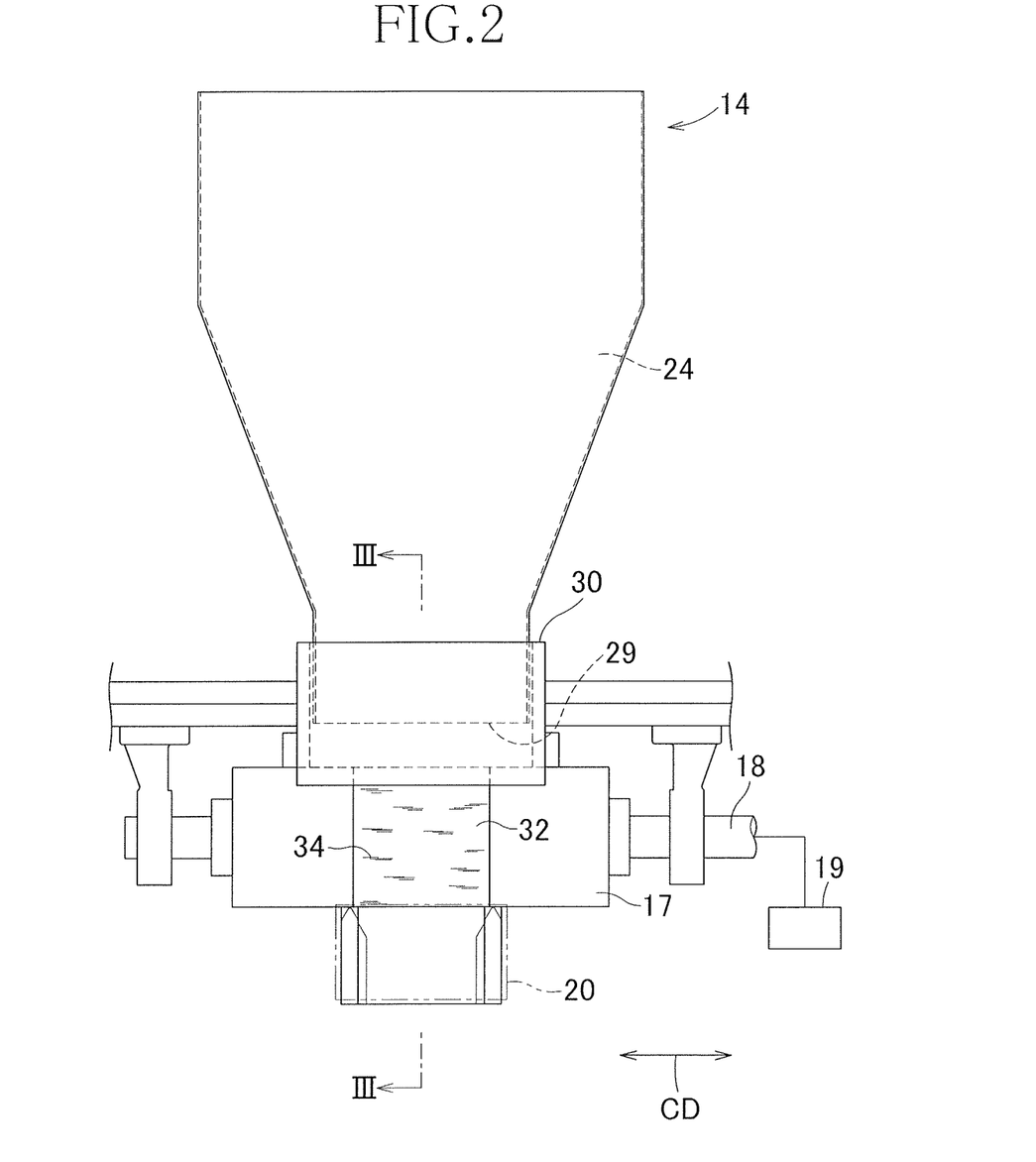
FIG. 2 is a front elevational view of an intermittent feeder.
Figure 3:
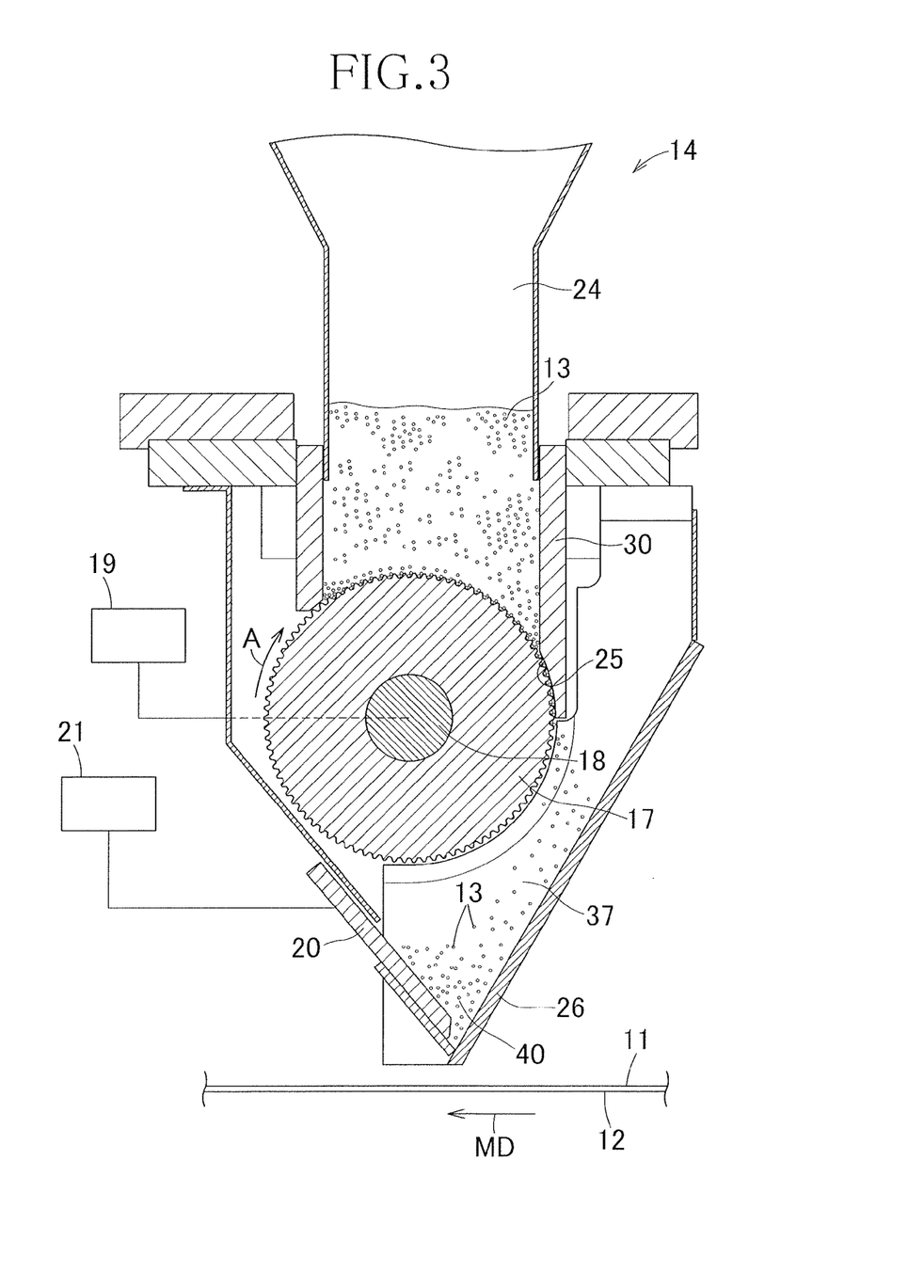
FIG. 3 is a sectional view taken along line in FIG. 2.
Figure 4:
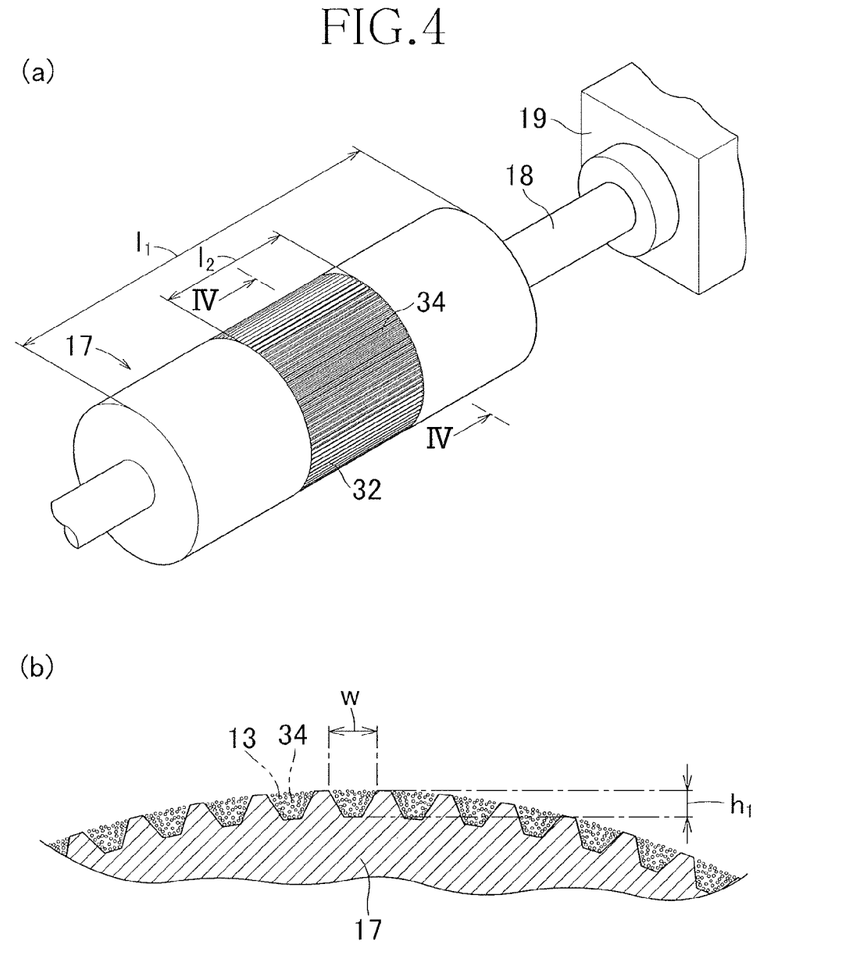
Figure 5:
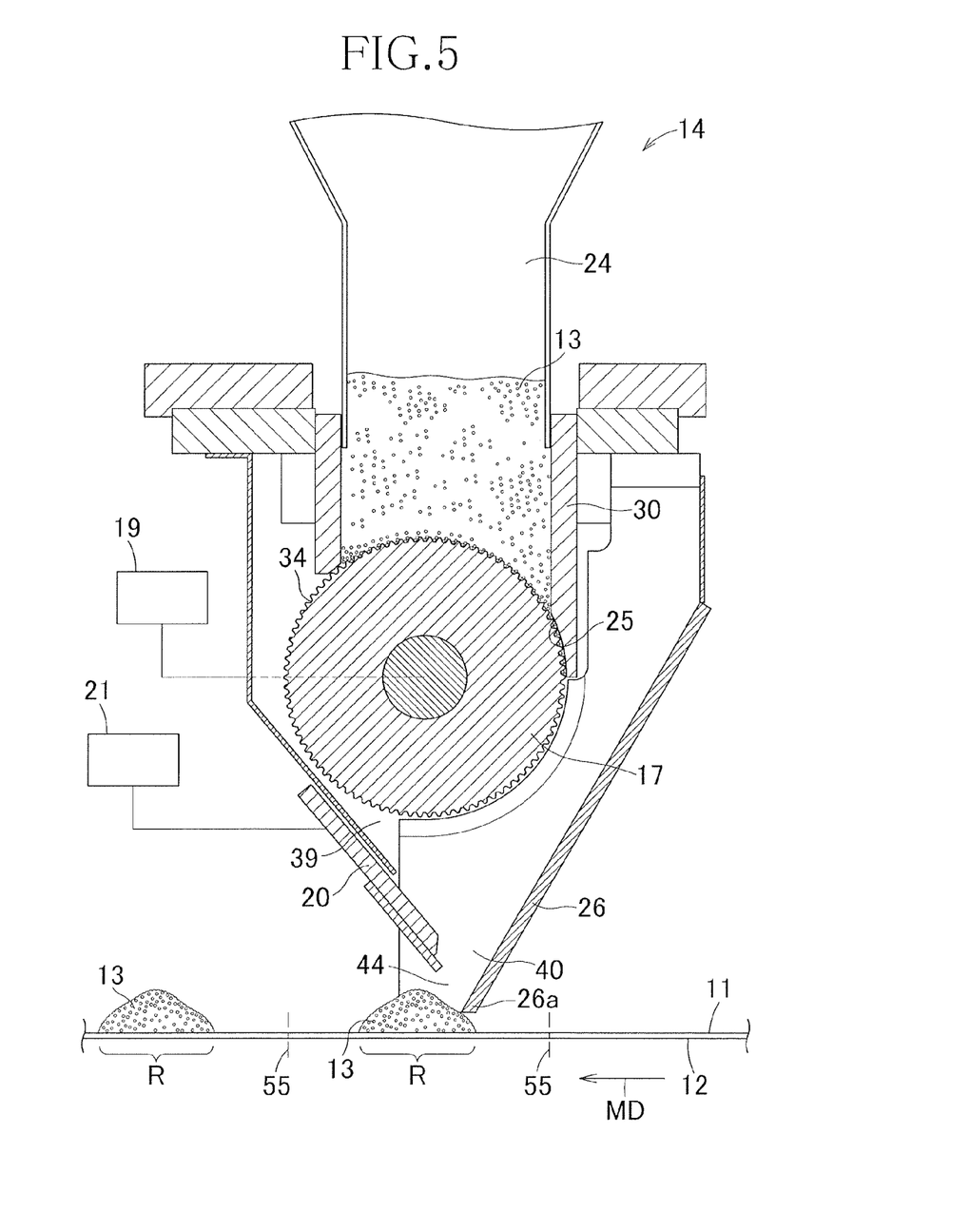
FIG. 5 is a sectional view similar to FIG. 3, illustrating a manner in which absorbent discrete material is intermittently fed.
Figure 6:
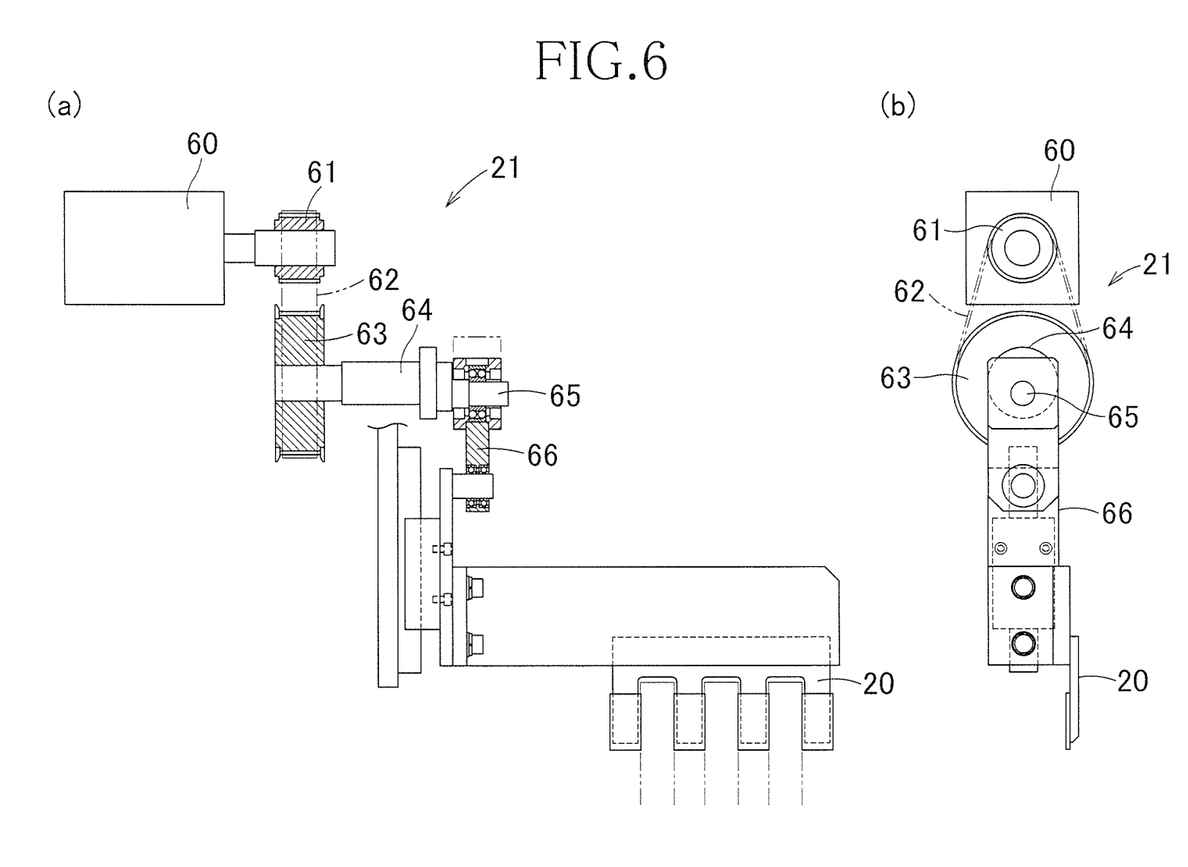

FIG. 1 is a diagram schematically illustrating an absorbent structure manufacturing apparatus 10 according to a first embodiment of this invention. FIG. 2 is a front elevational view of a feeder 14. FIG. 3 is a sectional view taken along line III-III in FIG. 2. FIG. 4($a$) is a perspective view of a measuring roller 17, FIG. 4($b$) is a sectional view taken along line IV-IV in FIG. 4($a$). FIG. 5 is a sectional view similar to FIG. 3, illustrating a manner in which absorbent discrete material 13 is intermittently fed. FIG. 6($a$) is a partially scale-enlarged diagram illustrating an open-close actuator means 21 and FIG. 6($b$) is a partially cutaway sectional view of the open-close actuator means 21. In this regard, a machine direction of the absorbent structure manufacturing apparatus 10 is designated by MD in FIG. 1 and a direction orthogonal to the machine direction MD is designated by CD in FIG. 2. In FIG. 4($b$), the absorbent discrete material 13 is indicated by imaginary lines for convenience of illustration.

Referring to FIG. 1, the absorbent structure manufacturing apparatus 10 includes a porous conveyor belt 12 serving to convey a continuous sheet 11 as a fibrous web in the machine direction MD and a feeder 14 adapted for intermittent feeding of an absorbent discrete material 13 such as superabsorbent polymer particles onto predetermined positions on the continuous sheet 11. Below the conveyor belt 12, a suction box 15 is provided so as to be opposed to the feeder 14 behind the conveyor belt 12. A rotary shaft of a rotary cutter 54 located downstream of the conveyor belt 12 is provided with a velocity detector means 16, for example, in the form of an rotary encoder so that a velocity detection signal $S_3$ output from the velocity detector means 16 may be input to a control unit 22. Rotary drive means adapted for rotary drive of a measuring roller 17 of the intermittent feeder 17 through the intermediary of a rotary shaft 18 and the open-close actuator means 21 adapted to open or close a shutter 20 through the intermediary of a cam mechanism also receives control signals $S_1$, $S_2$, respectively. In this regard, it is also possible to provide the velocity detector means 16 on upstream side and/or downstream side of the conveyor belt 12 instead of setting it in the rotary shaft of the rotary cutter 54. Alternatively, it is also possible to preprogram a predetermined conveyance velocity of the conveyor belt 12 in the control unit 22.

Referring to FIGS. 2 and 3, the intermittent feeder 14 includes: a hopper (material feeding space) 24 serving as a temporary reservoir of the absorbent discrete material 13; the measuring roller 17 serving to receive and to convey the absorbent discrete material 13 discharged from the hopper 24; a scraper 25 set up along an outer peripheral surface of the measuring roller 17; a feeding guide 26 functioning to guide the absorbent discrete material 13 toward the predetermined positions on the continuous sheet 11; the shutter 20 operating so that the absorbent discrete material 13 may be intermittently fed and a feed chute 40 adapted for temporary retention of the absorbent discrete material 13 dropped from the measuring roller 17.

The hopper 24 has an upper opening and a lower opening (outlet) 29 and the absorbent discrete material 13 in conduit (not shown) is poured through the upper opening into the hopper 24 and reserved therein. The absorbent discrete material 13 reserved within the hopper 24 is discharged through the lower opening 29 and deposited on the measuring roller 17. Between the hopper 24 and the measuring roller 17, there is provided a casing 30 to surround and thereby to retain the absorbent discrete material 13 deposited on the measuring roller 17.

Referring to FIG. 4, the measuring roller 17 is formed with a filling region on outer peripheral surface including a plurality of filling grooves 34 extending in the cross direction CD and is controllably rotated through the intermediary of the rotary shaft 18 in one direction (in a clockwise direction A in FIG. 3). More specifically, the rotary shaft 18 of the measuring roller 17 is in coaxial relationship with a servomotor as the rotary drive means 19 so that the rotary drive of the measuring roller 17 may be controlled by rotation of the servomotor. Each of the filling grooves 34 is dimensioned so as to be filled with a predetermined amount of the absorbent discrete material 13. Specifically, a length dimension $l_1$ of the measuring roller 17 is in a range of about 200 to about 250 mm, a length dimension $l_2$ of the filling region 32 is in a range of about 50 to about 70 mm, a width dimension w of the respective filling grooves 34 is in a range of 2.0 to 3.5 mm and a depth dimension $h_1$ thereof is in a range of 1.0 to 2.0 mm. In this regard, the shape and size of the filling grooves 34 are not limited to those specified in this embodiment but may appropriately varied depending on a given amount of the absorbent discrete material 13 with which the respective filling grooves 34 are to be filled.

The respective filling grooves 34 extend in a direction orthogonal to the direction A in which the measuring roller 17 rotates, i.e., in the cross direction CD. In the measuring roller 17 having such filling grooves 34, the absorbent discrete material 13 once filled in the filling grooves 34 should not spill out therefrom even when the measuring roller 17 rotates. In consequence, it is possible for these filling grooves 34 to be filled with and to retain a predetermined amount of the absorbent discrete material 13 and then to feed this predetermined amount of the absorbent discrete material 13 to the feed chute 40. The filling grooves 34 are arranged on the outer peripheral surface of the measuring roller 17 continuously in a circumferential direction thereof and therefore the predetermined amount of the absorbent discrete material 13 may be stably fed independently of a rotational position of the measuring roller 17. In addition, merely by adjusting the number of rotations and the rotational velocity of the measuring roller 17, the amount of the absorbent discrete material 13 may be arbitrarily varied without changing the measuring roller 17.

The scraper 25 is defined by part of the inner peripheral surface of the casing 30 at a lower end portion thereof so that the scraper 25 may be curved along the outer peripheral surface of the measuring roller 17. The scraper 25 extending along a portion of the outer peripheral surface of the measuring roller 17 in this manner assures that a surplus amount of the absorbent discrete material 13 filling the respective filling grooves of the measuring roller 17 is scraped away and left behind within the casing 30 and only the predetermined amount of the absorbent discrete material 13 filling the respective filling grooves 34 is dropped into the feed chute 40. In this regard, the placement of the scraper 25 and clearance between the scraper 25 and the measuring roller 17 may be changed by installing the casing 30 adjustably in the vertical direction. While the scraper 25 is integral with the casing 30 according to this embodiment, it is also possible to form the scraper 25 separately of the casing 30.

Referring to FIGS. 2 and 3, the shutter 20 is opened or closed under a control of the open-close actuator means 21. The shutter 20 cooperates with the feeding guide 26 and a peripheral wall 37 extending from a rim of the feeding guide 26 to define the feed chute 40 serving for temporary storage of the absorbent discrete material 13 dropping from the measuring roller 17.

With reference to FIGS. 1 through 5, a process of manufacturing an absorbent structure 41 with the absorbent structure manufacturing apparatus 10 having the aforementioned configuration will be described hereunder. First, the continuous sheet 11 is reeled out from a first feed roll 42 and conveyed by the conveyor belt 12 in the machine direction MD. Then, above the suction box 15, the absorbent discrete material 13 is intermittently fed from the feeder 14 onto the continuous sheet 11.

In the feeder 14, the absorbent discrete material 13 in the hopper 24 is discharged through the outlet 29 of the hopper 24 and deposited on the measuring roller 17 wherein a part of such absorbent discrete material 13 fills the respective filling grooves 34 of the measuring roller 17. The measuring roller 17 is rotating in one direction (clockwise direction A) at the rotational velocity corresponding to the velocity of the conveyor belt 12 and the absorbent discrete material 13 deposited on the outer peripheral surface of the measuring roller 17 is scraped off by the scraper 25 placed along the outer peripheral surface of the measuring roller 17 so that only the predetermined amount of the absorbent discrete material 13 is moved downward together with the filling grooves 34 without falling off from the respective filling grooves 34.

The surplus amount of the absorbent discrete material 13 having dropped off from the filling grooves 34 due to its own weight in the course of passing the scraper 25 is temporarily stored within the feed chute 40. Almost simultaneously when the predetermined amount of the absorbent discrete material 13 has been received by the feed chute 40, the shutter 20 is opened and the predetermined amount of the absorbent discrete material 13 is guided by a distal end portion 26a of the feeding guide 26 so as to be fed through a feed opening 44 onto the continuous sheet 11 being conveyed in the machine direction MD. The measuring roller 17 is being rotated in the direction A at a constant velocity corresponding to the conveyance velocity of the continuous sheet 11 and, in the fashion similar to the measuring roller 17, the shutter 20 is also open-close controlled at the frequency corresponding to the conveyance velocity of the continuous sheet 11. Immediately after the predetermined amount of the absorbent discrete material 13 has been fed onto the continuous sheet 11, the shutter 20 is closed and a next batch of the predetermined amount of the absorbent discrete material 13 is stored within the feed chute 40 and simultaneously the shutter 20 is opened so that the predetermined amount of the absorbent discrete material 13 may be fed onto the given position on the continuous sheet 11. In this way, the measuring roller 17 is rotated at the velocity corresponding to the velocity of the continuous sheet 11 and the shutter 20 is alternately open-close controlled at the frequency corresponding to the velocity of the continuous sheet 11. Thus, the predetermined amount of the absorbent discrete material 13 may be fed intermittently in the machine direction MD onto the predetermined position of the continuous sheet 11. In view of the fact that, after the predetermined amount of the predetermined amount of the absorbent discrete material 13 has been stored within the feed chute 40, the shutter 20 is opened and the predetermined amount of the absorbent discrete material 13 is fed onto the continuous sheet 11, the predetermined amount of the absorbent discrete material 13 may be intermittently fed onto the given position on the continuous sheet 11 in the deposited state.

The absorbent discrete material 13 is deposited on the continuous sheet 11 roughly in the center thereof as viewed in the width direction (i.e., in the cross direction CD) to define a feed target region R. Considering the amount of the absorbent discrete material 13 to be fed at once and the filling capacity of the respective filling grooves 34 of the measuring roller 17, when superabsorbent polymer particles are used as the absorbent discrete material 13, the average particle diameter thereof is preferably in a range of 200 to 500 um, more preferably in a range of 250 to 400 um.

After the absorbent discrete material 13 has been fed onto the continuous sheet 11, a continuous liner sheet 52 in the form of fibrous web unreeled from a second feed roll 50 and having a surface coated by adhesive supply means 51 with a hot melt adhesive is lapped on and bonded to the continuous sheet 11 to form a continuous composite sheet 53. The composite sheet 53 is cut by the rotary cutter 54 along a cut line 55 to obtain a plurality of the absorbent structures 41.

In the absorbent structure manufacturing apparatus 10 configured as has been described above, the absorbent discrete material 13 is fed onto the respective absorbent structure 41 roughly in the center thereof as viewed in the width direction (i.e., in the cross direction CD). Consequently, when the composite sheet 53 is cut by the rotary cutter 54 along the cut line 55, the absorbent discrete material 13 should not be present on and/or in the vicinity of the cut line 55 and should not interfere with the cut process.

As has previously been described, the measuring roller 17 and the shutter 20 are driven and actuated by the rotary drive means 19 and the open-close actuator means 21, respectively, wherein the respective cam mechanisms of the rotary drive means 19 and the open-close actuator mean 21 are partially formed of servomotors. The number of rotation and the rotational velocity of the respective servomotors are controlled by control signals $S_1$, $S_2$ input from the control unit 22. The control unit 22 receives the velocity detection signal $S_3$ output from the velocity detector means 16 attached to the rotary shaft of the rotary cutter 54 and sends control signals $S_1$, $S_2$ corresponding to the velocity of the continuous sheet 11 to the respective servomotors. As has previously been described, the respective servomotors operatively associated with the rotary drive means 19 and the open-close actuator means 21 are respectively driven and actuated in accordance with the conveyance velocity of the continuous sheet 11. For this reason, even if the conveyance velocity, i.e., the feed rate of the continuous sheet 11 changes, it is possible to feed the absorbent discrete material 13 onto the predetermined positions on the continuous sheet 11 without interrupting the process. Additionally for the reason that the rotary drive means 19 and the open-close actuator means 21 are controlled by the separate servomotors, only the rotational velocities of respective servomotors may be adjusted to change the number of rotations and the rotational velocity of the measuring roller 17 and thereby to change the amount of the absorbent discrete material 13 to be at once. Furthermore, the open-close timing maybe appropriately changed to predetermine the spacing between the adjacent feed target regions R arbitrarily. Even when the particle size such as the particle diameter is not uniform of the absorbent discrete material, the rotational velocity of the measuring roller 17 may be changed to assure the predetermined amount of the absorbent discrete material 13 to be intermittently fed without need to change the measuring roller 17. In this regard, this invention is not limited to this embodiment and it is also possible to control the rotational velocity of the measuring roller 17 in response to the conveyance velocity of the continuous sheet 11 indicated by the velocity detection signal $S_3$ output from the velocity detector means 16 and to control the timing in which the open-close of the shutter 20 by the open-close actuator means 21 in accordance with this detected rotational velocity.

Referring to FIG. 6(a) and FIG. 6(b), the open-close actuator means 21 is the cam mechanism utilizing a servomotor 60 adapted to be controlled by a cam program installed in the control unit 22 and including a first gear 61 rotary driven by the servomotor 60, a second gear 63 operatively associated with the first gear 61 by the intermediary of an endless belt 62 and an arm 66 coupled to the second gear 63 by the intermediary of a shaft 65 which is eccentric with respect to a rotary shaft 64 of the second gear 63. Though not illustrated, the first and second gears 61, 63 are formed on respective outer peripheral surfaces thereof with gear teeth and the endless belt 62 is formed on its inner surface with teeth adapted to be engaged with the gear teeth of the first and second gears 61, 63 so that the first and second gears 61, 63 may be rotated in operative association with the endless belt 62. The shutter 20 is connected to a distal end of the arm 66 and the rotational movement of the first and second gears 61, 63 in one direction caused by the servomotor 60 is converted to a linear movement of the arm 66 in vertical direction so as to open and to close the shutter 20. In this regard, it is not essential for the open-close actuator means 21 to utilize the cam mechanism so long as the open-close operation of the shutter 20 is compatible with the conveyance velocity of the continuous sheet 11.

<Second Embodiment>

Figure 7:
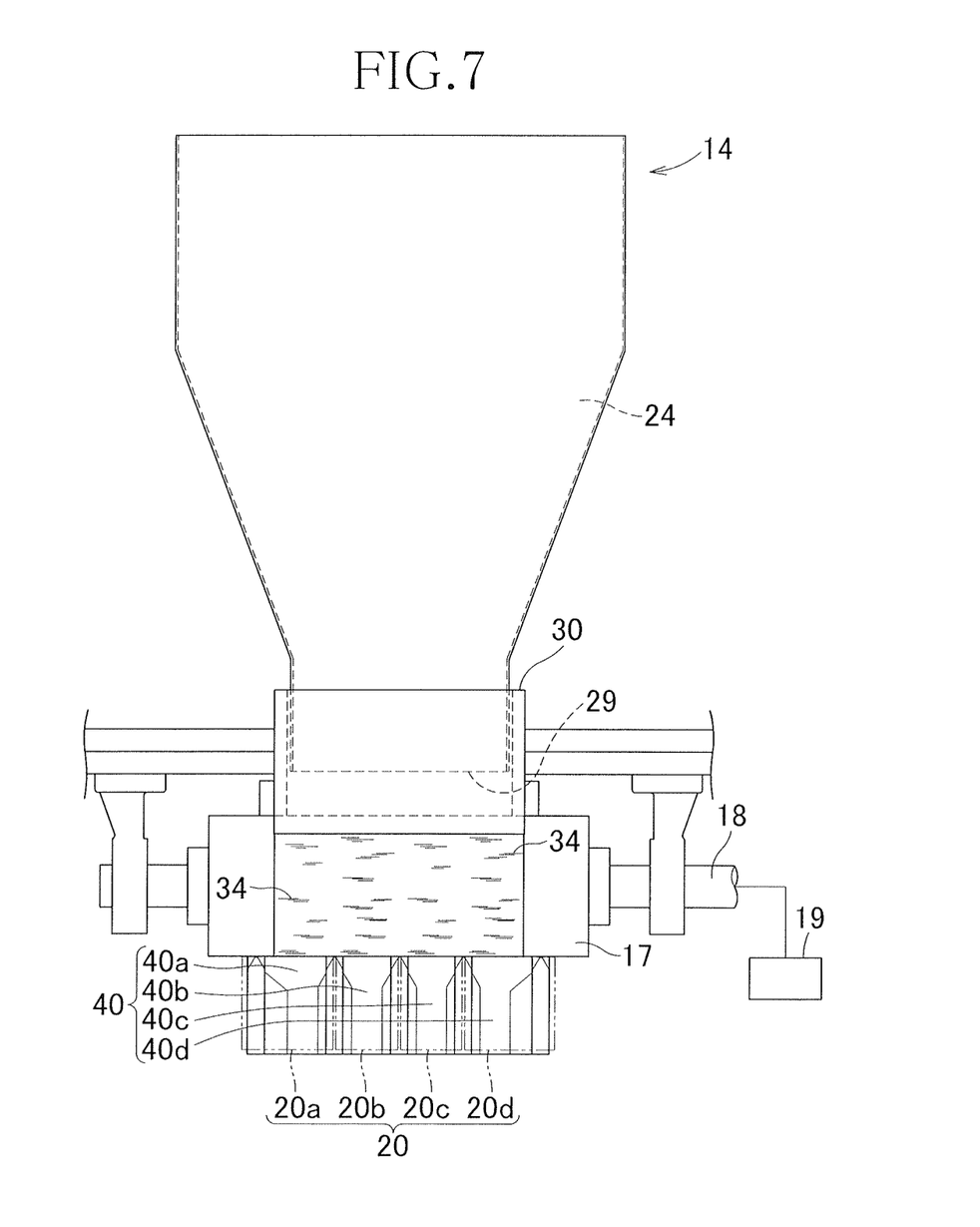
FIG. 7 is a front elevational view illustrating the intermittent feeder used in a second embodiment of this invention.
Figure 8:
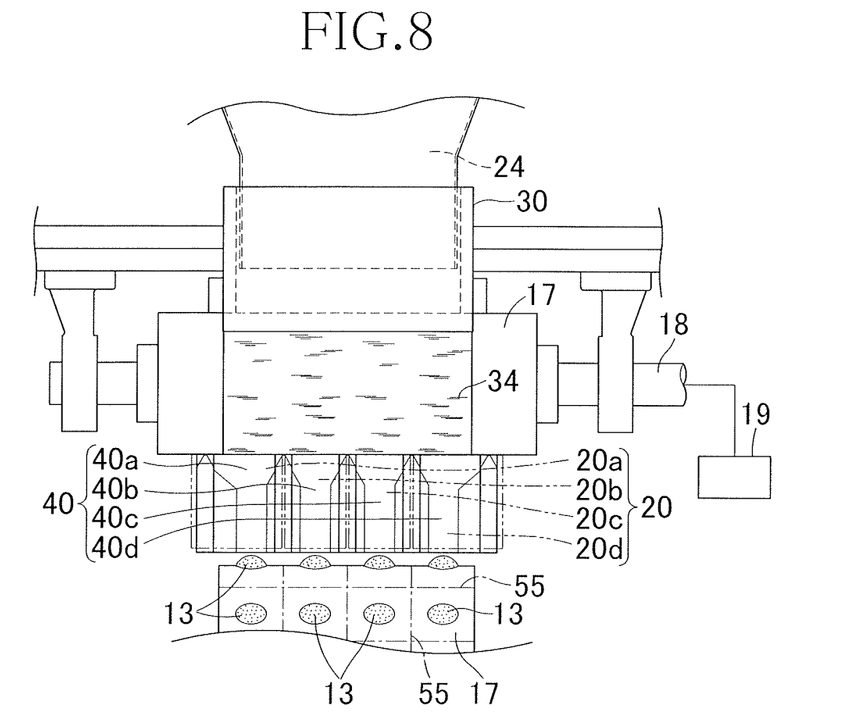
FIG. 8 is a partially scale-enlarged view of the absorbent structure manufacturing apparatus according to the second embodiment of this invention.
Figure 9:
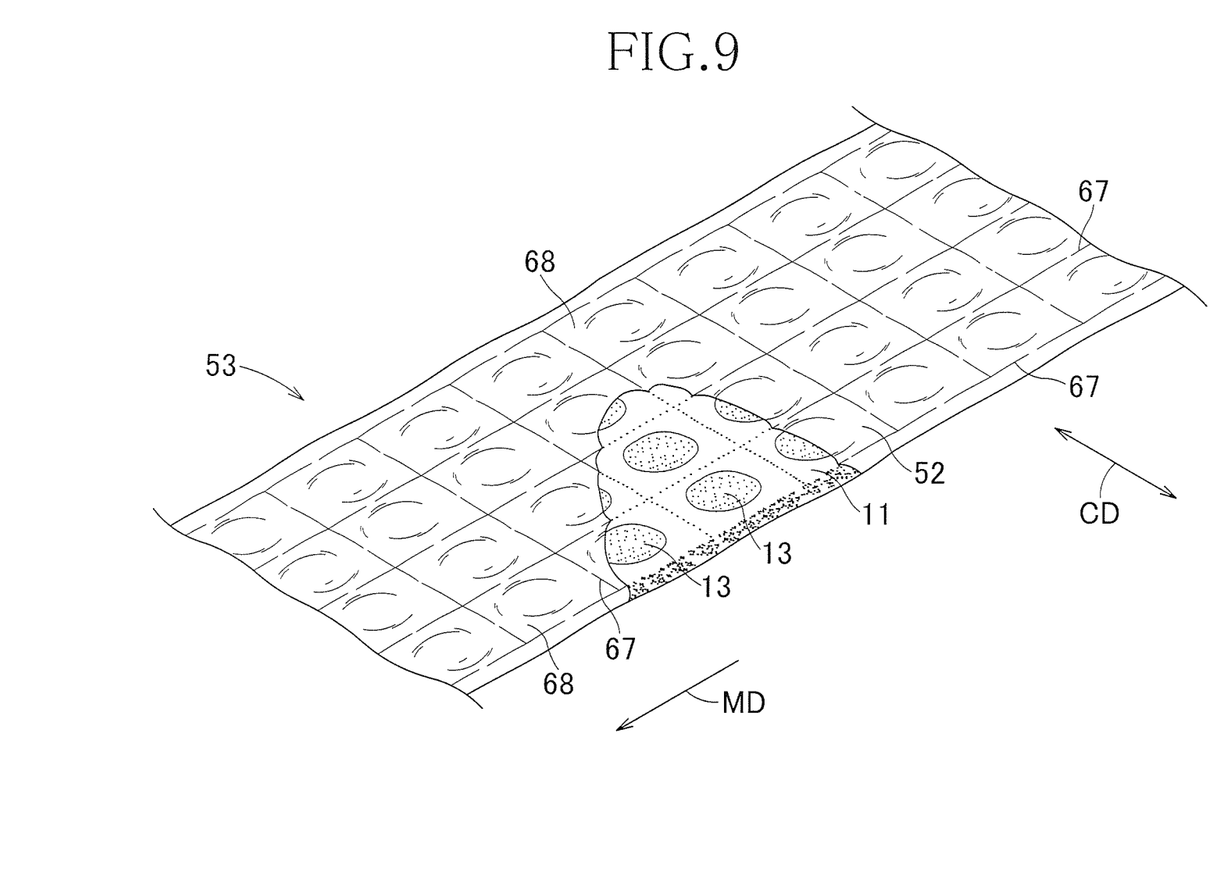
FIG. 9 is a partially cutaway perspective diagram illustrating a composite sheet obtained by the apparatus according to the second embodiment.

FIG. 7 is a front elevational view of the feeder 14 in a second embodiment of this invention, FIG. 8 is a partially scale-enlarged diagram illustrating the absorbent structure manufacturing apparatus 10 according to the second embodiment, and FIG. 9 is a partially cutaway perspective view illustrating the composite sheet 53 obtained by the apparatus according to the second embodiment. In this regard, the basic configuration of the absorbent structure manufacturing apparatus 10 according to this embodiment is substantially similar to that according to the first embodiment and, in view of this, only the aspect distinguished from the first embodiment will be described hereunder.

According to this embodiment, the feed chute 40 is divided into a plurality sections 40a, 40b, 40c, 40d arranged in the cross direction CD and the shutter 20 also is divided into a plurality of sections 20a, 20b, 20c, 20d in the cross direction CD so as to be operatively associated with the corresponding feed chute sections 40a, 40b, 40c, 40d.

With the feed chute 40 and the shutter 20 respectively divided into the plurality of sections arranged in the cross direction CD, it is possible to feed the absorbent discrete material 13 onto the predetermined positions on the continuous sheet 11 intermittently arranged in columns and rows in the machine direction MD and in the cross direction CD, respectively. More specifically, according to this embodiment, the continuous sheets 11, 52 are sealed together along seal lines 67 formed of sealing means so that the respective accumulations of the absorbent discrete material 13 may be surrounded by these seal lines 67 and thereby the composite sheet 53 defining a plurality of cells 68 retaining therein the respective accumulations of the absorbent discrete material 13. In an individual absorbent structure 41 having a plurality of the envelope-like compartment 68 obtained by cutting the composite sheet 53, the predetermined amount of absorbent discrete material 13 is retained in each of the cells 68 and it is assured that the absorbent discrete material 13 may be retained and evenly distributed in the respective compartments 68. In this regard, while it is also possible to feed the absorbent discrete material 13 in a reticular pattern as illustrated in FIG. 9, by dividing only the shutter 20 in a plurality of sections, there is a possibility that the amount of the absorbent discrete material 13 may be unevenly distributed into the respective cells 68. This is because the absorbent discrete material 13 dropping from the respective filling grooves 34 of the measuring roller 17 comes into collision with the single feed guide 26 and is guided into the respective sections 20a, 20b, 20c, 20d of the shutter 20. In contrast, not only the shutter 20 but also the feed chute 40 is divided into a plurality of the sections according to this embodiment so that the predetermined amount of the absorbent discrete material 13 may be evenly fed and distributed. In addition, while the respective accumulations of the absorbent discrete material 13 are evenly spaced apart from each other in the machine direction MD as well as in the cross direction CD as illustrated in FIG. 9, it is also possible to feed the absorbent discrete material 13 onto the continuous sheet 11 in various placement patterns, for example, in a zigzag pattern by selectively changing the shape of the filling grooves 34, the shape and the open-close timing of the shutter 20 and the shape of the feed chute 40.

<Third Embodiment>

Figure 10:
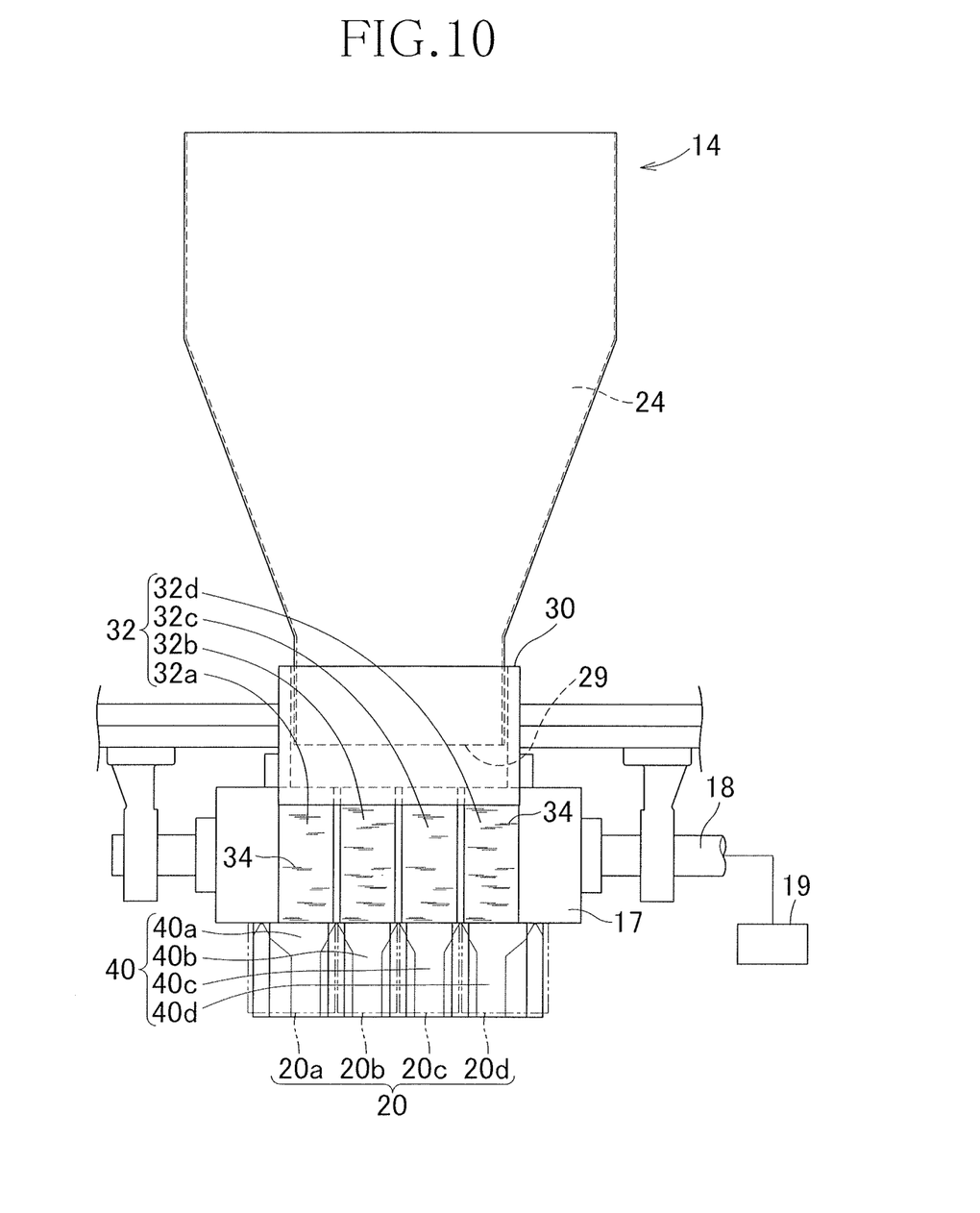
FIG. 10 is a front elevational view of the intermittent feeder used in a third embodiment of this invention.

FIG. 10 is a front elevational view similar to FIG. 7, illustrating the feeder 14 in a third embodiment of this invention.

According to this embodiment, the filling region 32 is divided into a plurality of sections 32a, 32b, 32c, 32d arranged in the cross direction CD and, though not illustrated, the scraper 25 also is divided into the sections corresponding to the respective sections of the filling region 32. The feed chute 40 and the shutter 20 are also divided into a plurality of sections arranged in the cross section CD so as to be associated with the corresponding filling sections 32a, 32b, 32c, 32d of the filling region so that the absorbent discrete material 13 flowing from the respective filling sections 32a, 32b, 32c, 32d so as to evenly distributed may be temporarily stored and then fed onto the continuous sheet.

According to this embodiment, it is possible to manufacture the composite sheet 53 having a plurality of cells 68 partitioned from each other as illustrated in FIG. 9 in a similar fashion to the second embodiment. This embodiment is distinguished from the second embodiment in which not only the feed chute 40 and the shutter 20 but also the filling region 32 also is divided so that the predetermined amount of the absorbent discrete material 13 may be more evenly distributed in the cross direction CD. In this regard, in order that the predetermined amount of absorbent discrete material 13 may be more accurately and evenly distributed, the width dimension (the dimension in the cross direction CD) of the respective sections 32a, 32b, 32c, 32d is preferably smaller than that of the feed chute 40.

<Fourth Embodiment>

Figure 11:
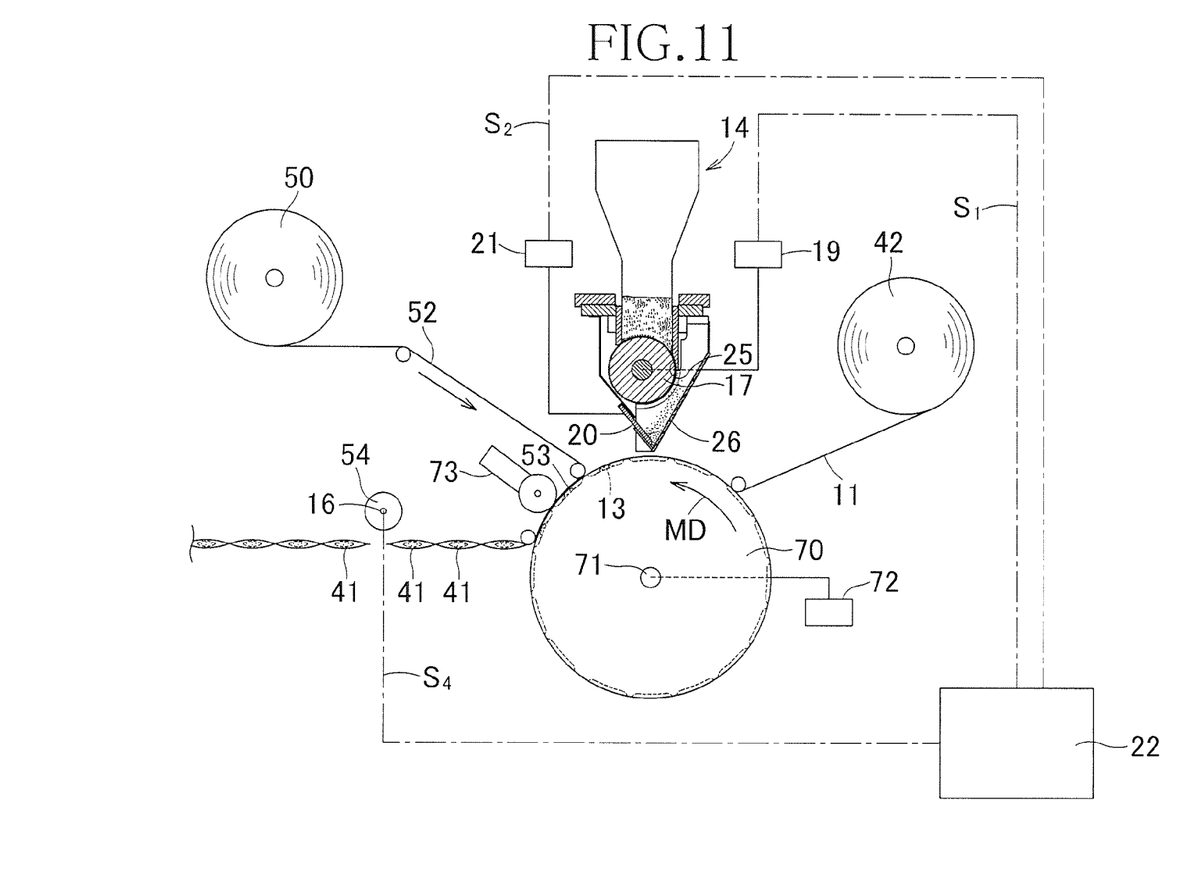
FIG. 11 is a diagram schematically illustrating the absorbent structure manufacturing apparatus according to a fourth embodiment of this invention.

FIG. 11 is a schematic diagram illustrating the absorbent structure manufacturing apparatus 10 according to a fourth embodiment of this invention. The basic configuration of the absorbent structure manufacturing apparatus 10 according to this embodiment is substantially similar to that according to the first embodiment and, in view of this, only the aspect distinguished from the first embodiment will be described hereunder.

According to this embodiment, the continuous sheet 11 is conveyed in the machine direction MD not by the rectilinear conveyor belt 12 but by a rotary drum 70 provided with a suction mechanism and feeding of the absorbent discrete material 13, bonding of the continuous sheet 11 to the continuous sheet 52 and cutting of the composite sheet 53 are carried out on the rotary drum 70. An outer peripheral surface of the rotary drum 70 is porous and the regions corresponding to the feed region R for the absorbent discrete material 13 are depressed inwardly so as to facilitate the absorbent discrete material 13 to be deposited therein. Below these regions, there is provided a suction mechanism adapted to suck the continuous sheet 11. The continuous sheet 11 and the continuous sheet 52 are bonded to each other not by an adhesive coating means by a heat seal means 73 located above the rotary drum 70 to form the composite sheet 53. The rotary drum 70 is rotary driven by a servomotor 72 by the intermediary of a rotary shaft 71. The velocity detection signal $S_3$ output from the velocity detector means 16 is transmitted to the control unit 22, and the respective servomotors of the rotary drive means 19 and the open-close actuator means 21 are controlled by the respective control signals $S_1$, $S_2$ output from the control unit 22. According to this embodiment, the respective steps of absorbent structure manufacturing process may be carried out on the single rotary drum 70 and thereby a manufacturing space may be drastically reduced, the manufacturing apparatus may be simplified and the manufacturing cost may be correspondingly reduced. In this regard, it is not essential for this invention to rotary drive the rotary drum 70 by means of the servomotor 72 and it is also possible to attach the velocity detector means 16 to the rotary shaft of the rotary drum 70.

The invention claimed is:

1. An absorbent structure manufacturing apparatus including a feeder adapted for intermittent feeding of absorbent discrete material onto continuous sheet continuously conveyed in a machine direction, wherein:
   the feeder includes:
   a measuring roller rotating in one direction and provided on an outer peripheral surface thereof with a filling region adapted to be filled with a predetermined amount of absorbent discrete material;
   a material feeding space adapted to reserve the absorbent discrete material on a steady basis and to feed the absorbent discrete material to the filling region of the measuring roller;
   a scraper located downstream of the feeder in the one direction so as to extend along a part of the outer peripheral surface of the measuring roller to fill the filling regions with only a predetermined amount of the absorbent discrete material fed in surplus to the filling region;

a feed chute adapted for receiving and temporarily retaining the absorbent discrete material having filled in the filling region and an open-close movable shutter forming a part of a peripheral wall defining the feed chute, wherein:

the measuring roller is rotary driven by rotary drive means in the one direction through the intermediary of a rotary shaft;

the shutter is opened and closed under control of open-close actuator means;

the rotary drive means and the open-close actuator means are electrically controlled by a control unit so that the rotary drive means rotates at a velocity corresponding to a conveyance velocity of the continuous sheet;

the open-close actuator means operates in association with the rotary drive means to open-close the shutter in a timing corresponding to the conveyance velocity; and the absorbent discrete material temporarily retained in the feed chute is intermittently fed onto the continuous sheet.

2. The absorbent structure manufacturing apparatus defined by claim 1, wherein the filling region is defined by a plurality of filling grooves extending in a direction crossing the machine direction.

3. The absorbent structure manufacturing apparatus defined by claim 2, wherein the filling grooves are continuously arranged on the outer peripheral surface of the measuring roller in a circumferential direction thereof.

4. The absorbent structure manufacturing apparatus defined by claim 1, wherein the apparatus includes velocity detector means adapted to detect the conveyance velocity of the continuous sheet so that the conveyance velocity detected by the velocity detector means is input to the control unit and a control signal in response to the conveyance velocity is transmitted from the control unit to the rotary drive means and the open-close actuator means.

5. The absorbent structure manufacturing apparatus defined by claim 1, wherein the rotary drive means is a servomotor.

6. The absorbent structure manufacturing apparatus defined by claim 1, wherein the feed chute and the shutter are respectively divided into two or more sections in the cross direction so that the absorbent discrete material is fed onto the continuous sheet intermittently in the machine direction as well as in the cross direction.

7. The absorbent structure manufacturing apparatus defined by claim 1, wherein the filling region defined on the measuring roller and the scraper are divided into two or more sections in the cross direction so that the feed chute and the scraper are respectively divided into two or more sections in the cross direction and the feed chute and the shutter are respectively divided into two or more sections so as to correspond to the respective sections of the divided filling region.

8. The absorbent structure manufacturing apparatus defined by claim 1, wherein the continuous sheet is conveyed by a rotary drum so that at least a step of feeding the absorbent discrete material by the feeder and a step of bonding another continuous sheet to the continuous sheet is carried out on the rotary drum.

* * * * *